United States Patent
Ohtomo et al.

(10) Patent No.: US 9,541,495 B2
(45) Date of Patent: Jan. 10, 2017

(54) IMAGE PICKUP DEVICE

(71) Applicant: Kabushiki Kaisha TOPCON, Itabashi-ku, Tokyo-to (JP)

(72) Inventors: Fumio Ohtomo, Asaka (JP); Hitoshi Otani, Tokyo-to (JP); Masayuki Momiuchi, Tokyo-to (JP); Kazuki Osaragi, Tokyo-to (JP)

(73) Assignee: Kabushiki Kaisha TOPCON, Tokyo-to (JP)

( * ) Notice: Subject to any disclaimer, the term of this patent is extended or adjusted under 35 U.S.C. 154(b) by 398 days.

(21) Appl. No.: 14/347,389

(22) PCT Filed: Sep. 20, 2012

(86) PCT No.: PCT/JP2012/074812
§ 371 (c)(1),
(2) Date: Mar. 26, 2014

(87) PCT Pub. No.: WO2013/047627
PCT Pub. Date: Apr. 4, 2013

(65) Prior Publication Data
US 2014/0232858 A1    Aug. 21, 2014

(30) Foreign Application Priority Data

Sep. 28, 2011 (JP) ................. 2011-212478
Oct. 20, 2011 (JP) ................. 2011-230443

(51) Int. Cl.
*G01N 21/25* (2006.01)
*G02B 5/20* (2006.01)
(Continued)

(52) U.S. Cl.
CPC ........... *G01N 21/255* (2013.01); *G01J 3/0229* (2013.01); *G01J 3/2823* (2013.01); *G01J 3/32* (2013.01);
(Continued)

(58) Field of Classification Search
CPC ............ G01J 3/10; G01J 3/0229; G01J 5/602; G02B 5/28; G02F 2203/055; G01N 21/255; H04N 5/332
See application file for complete search history.

(56) References Cited

U.S. PATENT DOCUMENTS

2003/0176768 A1   9/2003   Gono et al.
2005/0286760 A1   12/2005  Ohtomo et al.
(Continued)

FOREIGN PATENT DOCUMENTS

JP   4-125429 A    4/1992
JP   2002-34908 A  2/2002
(Continued)

OTHER PUBLICATIONS

International Search Report and Written Opinion mailed Nov. 6, 2012 in corresponding PCT application No. PCT/JP2012/074812.
(Continued)

*Primary Examiner* — Obafemi Sosanya
(74) *Attorney, Agent, or Firm* — Nields, Lemack & Frame, LLC

(57) ABSTRACT

An image pickup device, which comprises an optical characteristics changing unit (15), an optical system (45) containing an objective lens (47) and for leading a light from the objective lens to the optical characteristics changing unit, and an image pickup element (52) for receiving a light via the optical characteristics changing unit, wherein the optical characteristics changing unit has two or more dividing units, and has a configuration where one of the dividing units is selectively disposed along an optical path, and the dividing unit has a first region to select a specific wavelength from the light coming from the optical system and a second region where optical characteristics of the light from the optical system are not changed.

16 Claims, 13 Drawing Sheets

(51) Int. Cl.
| | |
|---|---|
| *H04N 9/04* | (2006.01) |
| *H04N 13/02* | (2006.01) |
| *G01J 3/28* | (2006.01) |
| *G02B 26/08* | (2006.01) |
| *H04N 5/33* | (2006.01) |
| *G01J 3/32* | (2006.01) |
| *G01J 3/02* | (2006.01) |
| *G01J 3/12* | (2006.01) |

(52) U.S. Cl.
CPC ............... *G02B 5/20* (2013.01); *G02B 26/08* (2013.01); *H04N 5/332* (2013.01); *H04N 9/045* (2013.01); *H04N 13/0221* (2013.01); *G01J 2003/1226* (2013.01); *G01J 2003/1243* (2013.01); *G01J 2003/2826* (2013.01); *H04N 2209/043* (2013.01)

(56) References Cited

U.S. PATENT DOCUMENTS

| | | | | |
|---|---|---|---|---|
| 2008/0292165 A1* | 11/2008 | El Fakhri | ............... | G06T 5/001 382/131 |
| 2009/0093700 A1* | 4/2009 | Hall | ............... | A61B 5/0059 600/407 |
| 2009/0244355 A1 | 10/2009 | Horie | | |
| 2010/0149536 A1 | 6/2010 | Sato | | |
| 2011/0007306 A1 | 1/2011 | Jak et al. | | |
| 2011/0074992 A1* | 3/2011 | Ajito | ............... | H04N 5/332 348/279 |
| 2011/0282578 A1* | 11/2011 | Miksa | ............... | G06F 17/30241 701/532 |

FOREIGN PATENT DOCUMENTS

| | | |
|---|---|---|
| JP | 2004279140 A | 10/2004 |
| JP | 2006-10376 A | 1/2006 |
| JP | 2009-258618 A | 11/2009 |
| JP | 2010254870 A | 10/2010 |
| JP | 2011-89895 A | 5/2011 |
| JP | 2011515675 A | 5/2011 |
| WO | 2005/046248 A1 | 5/2005 |
| WO | 2009028398 A1 | 3/2009 |

OTHER PUBLICATIONS

International Preliminary Report on Patentability mailed Apr. 10, 2014 in corresponding PCT application No. PCT/JP2012/074812.

\* cited by examiner

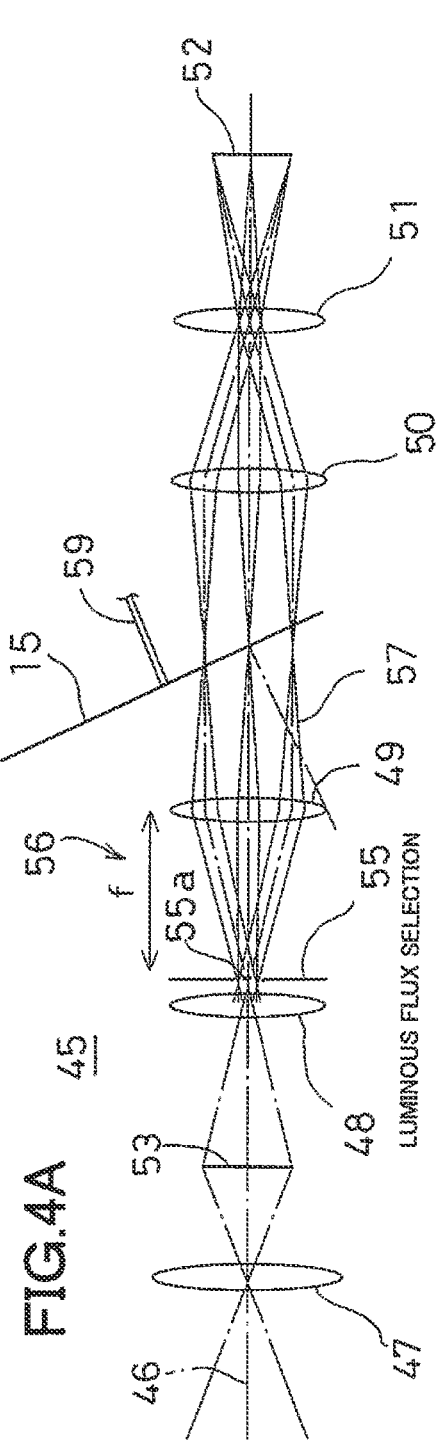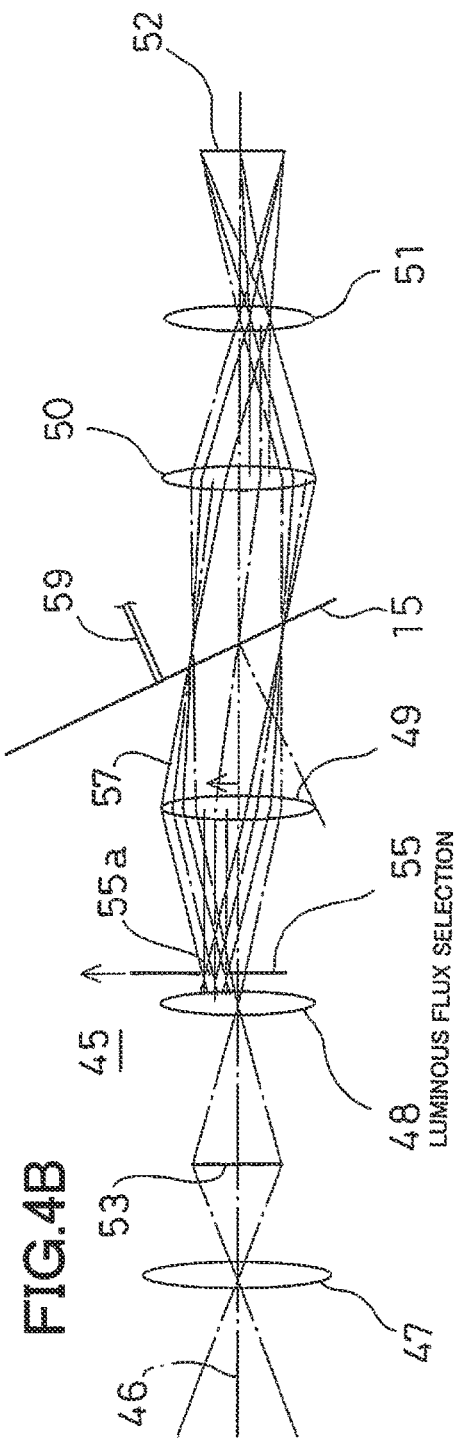

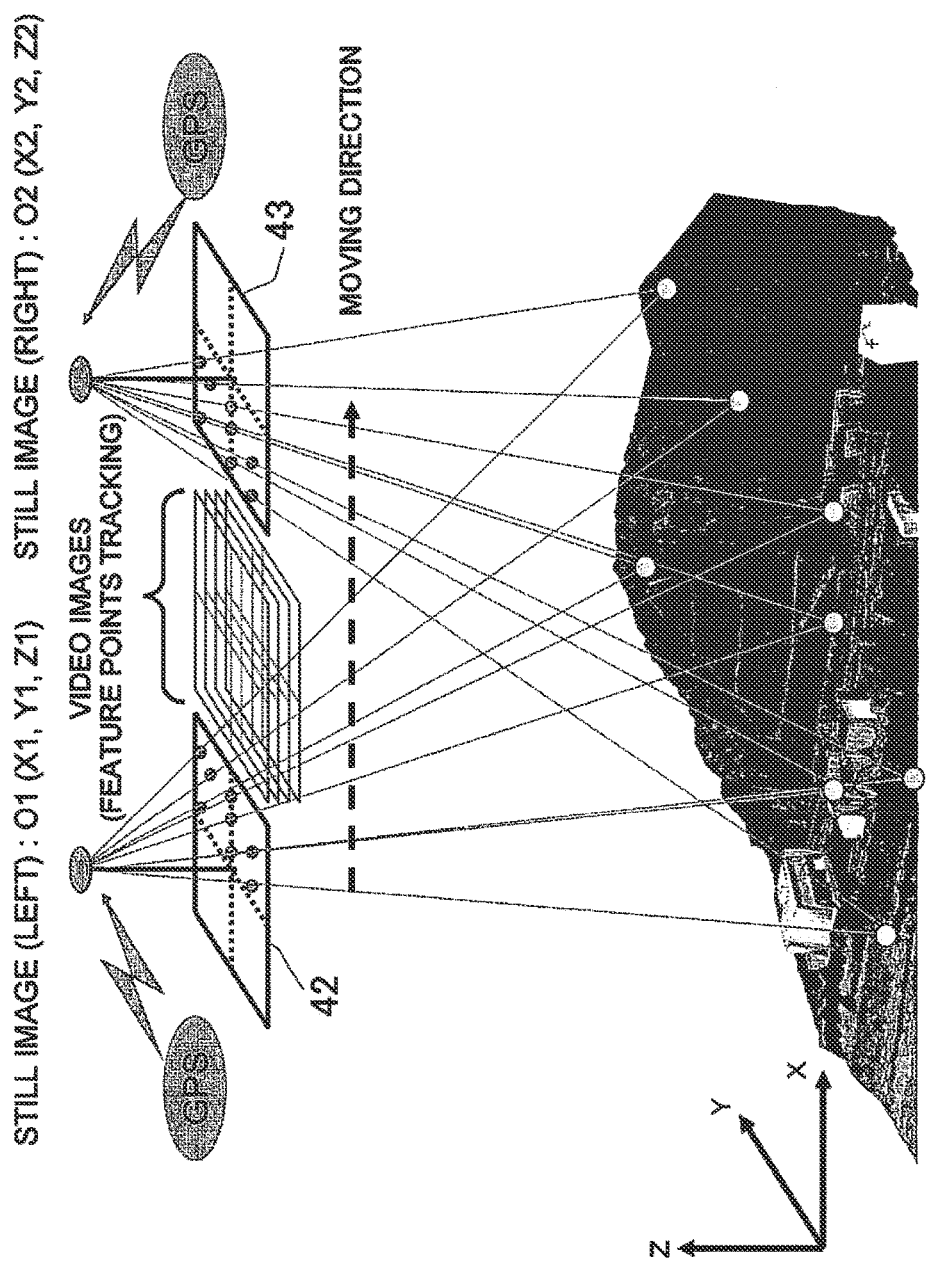

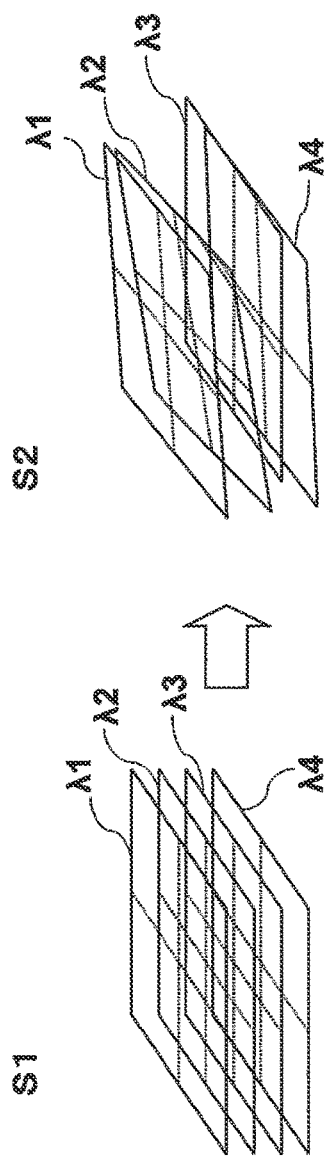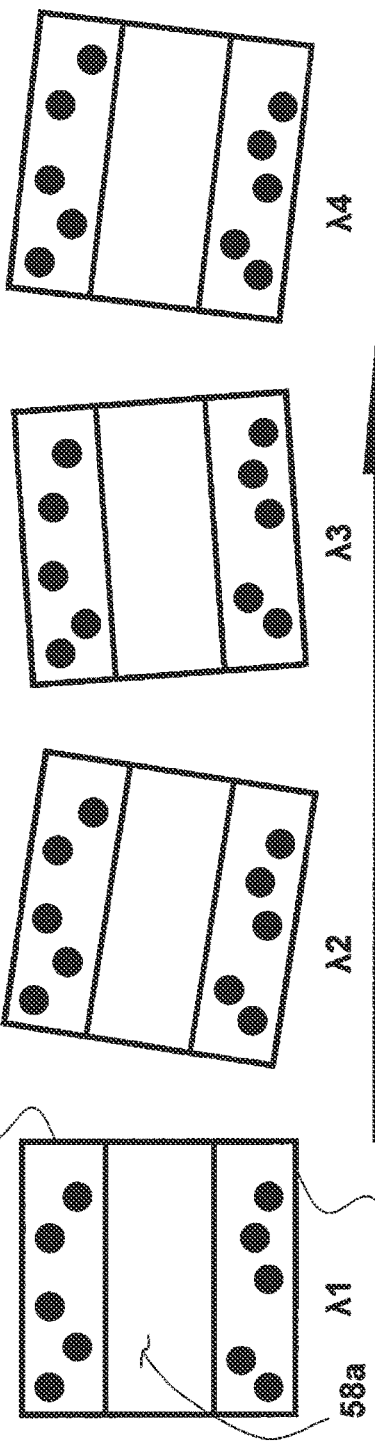

IMAGE PICKUP DEVICE

TECHNICAL FIELD

The present invention relates to an image pickup device to acquire optical spectral characteristics, and further, to acquire a hyper-spectral image of an object to be measured.

BACKGROUND ART

It has been practiced in the past to acquire an image of an object to be measured at the same time as the acquisition of three-dimensional data of the object to be measured, and to acquire three-dimensional data with image by carrying out digital photogrammetry of the object to be measured etc.

The three-dimensional data with images as acquired by a conventional type three-dimensional measuring device have been used for map data and the like, and it has been used to provide effects such as an effect to heighten user's visibility or any other effects.

On the other hand, the data acquired is three-dimensional position data of the object to be measured, and information thus acquired is a three-dimensional position of the object to be measured.

When measurement is performed on the object to be measured, it is wanted to acquire more types of information, and it is desirable that not only positional information of the object to be measured but also information on characteristics of the object to be measured, and a geographic information system (GIS) is utilized for this purpose.

For instance, if information on growing conditions of agricultural products can be acquired, adequate judgment and appropriate measures can be taken on agricultural work. Or, if type and other conditions of mineral substance exposed on ground surface can be identified, it is possible or the like to select a civil engineering operation method adequate for the purpose.

To attain the purposes as described above, the present invention provides an image pickup device, by which it is possible to acquire optical spectral characteristics—in particular, a hyper-spectral image.

PRIOR ART REFERENCES

[Patent Document 1] Patent Publication JP-A-2011-89895
[Patent Document 2] Patent Publication JP-A-2006-10376

DISCLOSURE OF THE INVENTION

The present invention relates to an image pickup device, which comprises an optical characteristics changing unit, an optical system containing an objective lens and for leading a light from the objective lens to the optical characteristics changing unit, and an image pickup element for receiving a light via the optical characteristics changing unit, wherein the optical characteristics changing unit has two or more dividing units, and has a configuration where one of the dividing units is selectively disposed along an optical path, and the dividing unit has a first region to select a specific wavelength from the light coming from the optical system and a second region where optical characteristics of the light from the optical system are not changed.

Further, the present invention relates to the image pickup device which further comprises an image pickup control device, wherein based on image matching of an image taken via the second region of one dividing unit and an image taken via the second region of another dividing unit, an optical spectral synthesized image is prepared by synthesizing an image taken via the first region of the one dividing unit with an image taken via the first region of another dividing unit.

Further, the present invention relates to the image pickup device which further comprises an aperture disposed along an optical path, wherein the aperture has an aperture orifice, and wavelength to be selected by the optical characteristics changing unit can be changed by moving the aperture.

Further, the present invention relates to the image pickup device, wherein the optical characteristics changing unit further comprises a still another dividing unit not to change optical characteristics of the first region and the second region.

Further, the present invention relates to the image pickup device, wherein, based on image matching of an image taken via the second region of two or more dividing units and a still image taken via the still another dividing unit, the image pickup control device synthesizes an image taken via the first region of two or more dividing unit and the still image and prepares a hyper-spectral image.

Furthermore, the invention relates to the image pickup device which further comprises a. GPS device for carrying out measurement of geocentric coordinates, wherein the image pickup control device acquires a still image via the still another dividing unit at a first point, extracts two or more feature points from the still image at the first point, acquires a video image containing a frame image continuous in time series via the still another dividing unit during the moving from the first point to the second point, and further performs video image tracking by a video image moving from the first point to the second point, acquires a still image via the still another dividing unit at the second point, specifies the feature point on the still image at the second point, carries out stereo-matching of the still image at the first point and the still image at the second point based on the feature point, prepares a three-dimensional model based on positions in an geocentric coordinate system of the first point and the second point measured by the GPS device, and the image pickup control device prepares a four-dimensional model having three-dimensional position data and optical spectrum information by synthesizing the optical spectral synthesized image and the three-dimensional model.

BRIEF DESCRIPTION OF THE DRAWINGS

FIG. 4A and FIG. 4B each represents an illustration to show optical system of a camera having a transmission type interference filter to be used in the embodiment of the present invention. FIG. 4A shows a condition where an aperture orifice concurs with an optical axis, and FIG. 4B shows a condition where the aperture orifice is separated from the optical axis.

FIG. 7 is an illustration to show a condition where a hyper-spectral image is acquired in the present embodiment.

FIG. 8 are illustrations to show a condition between images when a plurality of images are acquired in hovering state.

FIG. 11A shows a condition where an aperture orifice concurs with an optical axis, and FIG. 11B shows a condition where an aperture orifice is separated from the optical axis.

FIG. 13A shows a condition where the aperture orifice concurs with the optical axis, and FIG. 13B shows a condition where the aperture orifice is separated from the optical axis.

LEGEND OF REFERENCE NUMERALS

Figure 1:
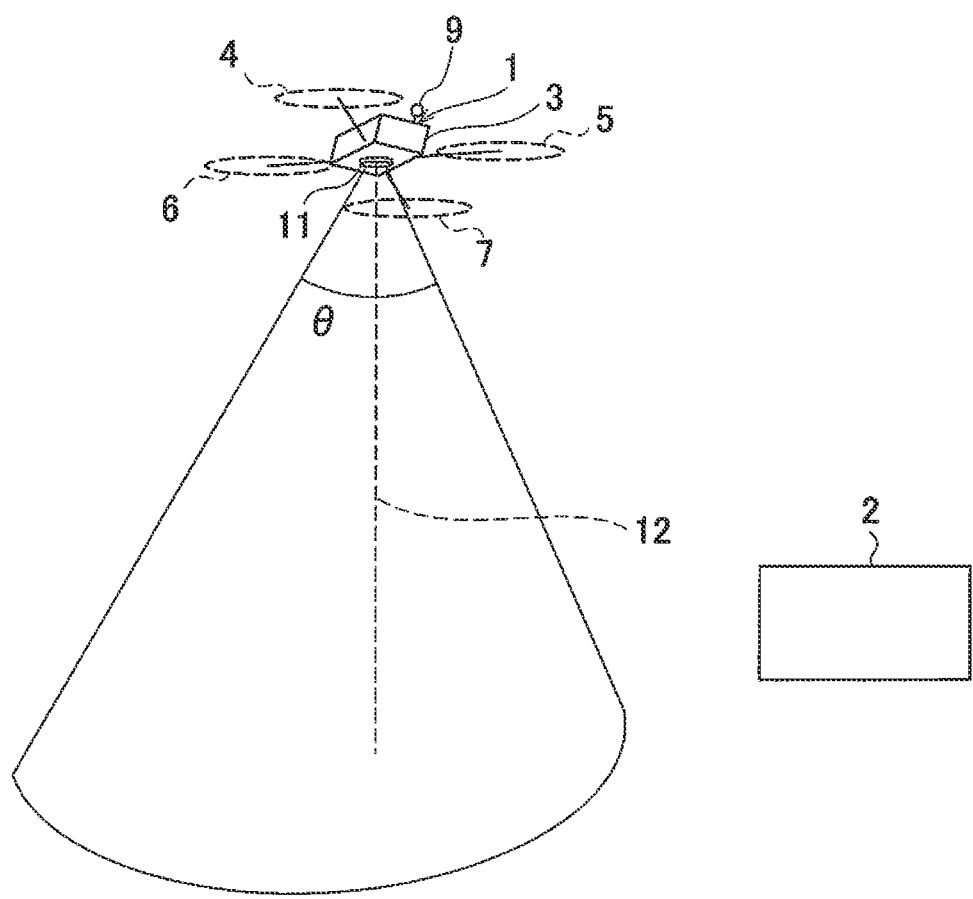
FIG. 1 is a schematical drawing to show a small flying object where an image pickup device according to the present invention is mounted on board.

1 Helicopter
2 Base station control device
3 Helicopter body
9 GPS device
11 Image pickup device
12 Optical axis
13 Camera unit
14 Camera.
15 Interference filter
21 Image pickup control device
22 Arithmetic control unit
28 Image synthesizing unit
29 Image processing unit
33 Measuring unit
34 Model image forming unit
35 Display unit
36 Storage unit
45 Optical system
47 Objective lens
48 First relay lens
49 Second relay lens
50 Third relay lens
51 Image forming lens
52 Image pickup element
55 Aperture
56 Telecentric optical system
57 Principal ray
58 Image
60 Divided transmission surface
61 Interference filter
62 Interference filter
63 Divided reflection surface
64 Reflection mirror

BEST MODE FOR CARRYING OUT THE INVENTION

Description will be given below on an embodiment of the present invention by referring to the attached drawings.

An image pickup device according to the embodiment of the present invention is mounted on board of a small type Unmanned Aerial Vehicles e.g. a small type helicopter which can be operated by remote control or a small type helicopter capable of carrying out autonomous flight.

FIG. 1 shows a small flying object 1 where an image pickup device according to the present embodiment is mounted on board.

In FIG. 1, reference numeral 2 represents a base station control device to be installed on ground surface. The base station control device 2 can be in data communication with a flying object 1 and control flight of the flying object 1, sets and changes flight plan, and stores and manages information collected by the flying object 1.

The flying object 1 is, for instance, a helicopter used as a small type flying object to be operated in autonomous flight. This helicopter is operated by remote control from the base station control device 2. Or, a flight plan is set up on a control device (not shown) of the helicopter 1 from the base station control device 2, and the control device controls navigation means (to be described later) and autonomous flight is performed according to a flight plan. Further, the control device controls the navigation means and controls the helicopter 1 so as to fly at a predetermined speed and at a predetermined altitude, and also can control the helicopter in hovering state (stationary flying condition) at a predetermined position.

The helicopter 1 has a helicopter body 3, and has many propellers as required and mounted on the helicopter body 3 e.g. four sets of propellers 4, 5, 6 and 7, each being mounted at front, rear, left and right positions respectively. Each of the propellers 4, 5, 6 and 7 is individually connected to a motor (not shown), and driving of each motor is designed to be controlled independently. The propellers 4, 5, 6 and 7 and the motors and the like make up together navigation means of the helicopter 1.

On the helicopter body 3, a GPS device 9 for measuring reference positions of the helicopter 1 (e.g. the center of the helicopter body 3) is mounted.

On the helicopter body 3 of the helicopter 1, an image pickup device 11 is provided on board. The image pickup device 11 has an optical axis 12, and the optical axis 12 is designed to be extended in downward direction so that the image pickup device 11 can take images of positions in downward direction of the helicopter 1.

Figure 2:
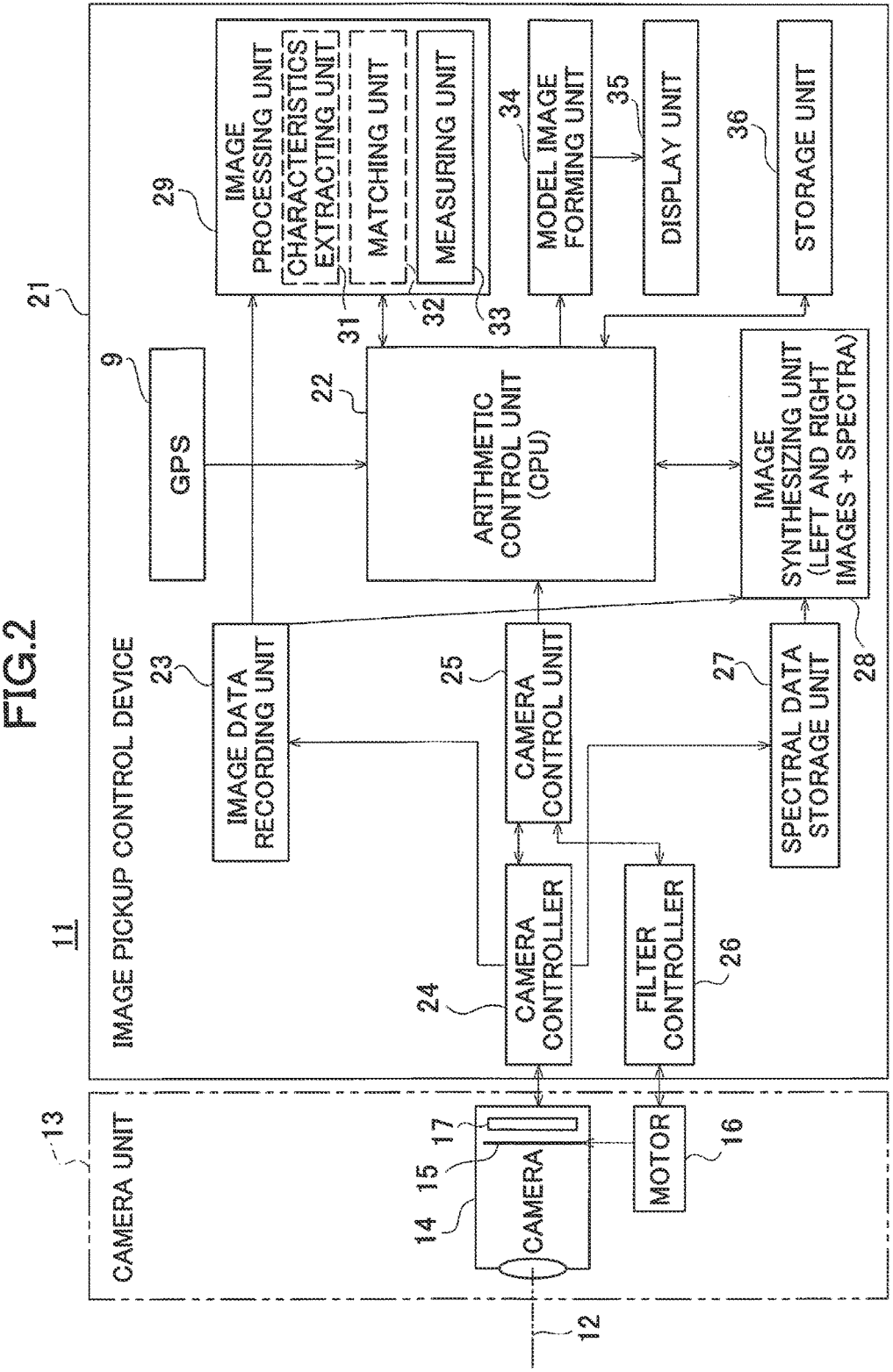
FIG. 2 is a schematical block diagram of a camera unit and an image pickup control device of the image pickup device according to a first embodiment of the present invention.

Next, referring to FIG. 2, description will be given on approximate arrangement of the image pickup device 11 according to a first embodiment of the present invention.

The image pickup device 11 has a camera unit 13 and an image pickup control device 21. The image pickup control device 21 can carry out digital photogrammetry on an object to be measured according to image data as picked up by the camera unit 13 and position information from the GPS device 9, or performs processing such as synthesizing of optical spectral image data acquired by the camera unit 13 with the image data and other.

First, description will be given on the camera unit 13.

The camera unit 13 comprises a camera 14, an interference filter 15, which is an optical characteristics changing unit as described later, and a motor 16 used as means to change over the interference filter 15. The camera 14 is provided along the optical axis 12 and is so designed that the camera 14 can acquire an image as it is (i.e. a real image) of the object no be measured and an optical spectral image.

The camera 14 takes images at the points to be measured and outputs digital image data. Also, the camera 14 can take a still image at a predetermined time interval, and can continuously take video images (i.e. video images constitute frame images, which are continuous in time series).

Further, the camera 14 has a CCD or CMOS sensor, which is an aggregate of pixels, as an image pickup element 17, and a relation between the optical axis 12 and the image pickup element 17 is set in such manner that the optical axis 12 perpendicularly passes through the center (i.e. the center of coordinates of a photodetection surface) of the image pickup element 17. Therefore, it is so designed that the position (coordinates) of each pixel of the image pickup element 17 can be specified on the image pickup element 17, and further, that a field angle of each pixel (i.e. an angle with respect to the optical axis 12) can be identified.

Further, the camera 14 has the interference filter 15 provided along the optical axis 12 and having interference membranes prepared on a part of the interference filter 15. The interference filter 15 is rotatably supported and can be rotated by the motor 16. The interference filter 15 has a plurality of divided units, each having different optical characteristics. Each of the divided units has a region where the interference membranes are prepared and also has a region, which has no optical characteristics. The divided units are selected when the interference filter 15 is rotated by the motor 16. It is designed so that the divided unit which is selected concurs with optical axis of the camera 14, the light passes through the divided unit as selected, further, a light with a predetermined wavelength and lights with all wavelengths are received at the same time on the image pickup element 17, depending on the divided units to pass through and an optical spectral image with the predetermined wavelength and a real image can be acquired by the camera 14 at the same time.

Next, referring to FIG. 3, description will be given below on details of the interference filter 15.

The interference filter 15 is a transmission type of interference filter. It is designed in shape of a circular disk as shown in FIG. 3. Transmission surface is equally divided (divided in 6 equal portions in the figure) at an angle as required in circumferential direction, and the divided unit is prepared as divided transmission surfaces 60*a* to 60*f*.

Among the divided transmission surfaces 60*a* to 60*f*, in the divided transmission surfaces 60*a* to 60*f*, which are a plurality of the divided units, a second region is formed concentrically, a first region is prepared inside the second region, and further, a second region is prepared on inner side of the first region. In the first region, transmission interference membranes having differently selected wavelength characteristics with selected wavelengths λ1 to λ5 are prepared for each of the divided transmission surfaces 60*a* to 60*e* respectively. Further, it is so arranged that the divided transmission surface 60*f*, which is another divided unit, has no optical characteristics in the first region and the second region (60*f'* and 60*f"*) so that all lights with any wavelength can pass through.

For instance, in the first region, a transmission interference membrane having selected wavelength λ1 of 400 nm-450 nm is formed on the divided transmission surface 60*a*. Similarly, a transmission interference membrane having a selected wavelength λ2 of 450 nm to 525 nm is formed on the divided transmission surface 60*b*, a transmission interference membrane having a selected wavelength λ3 of 525 nm to 650 nm is formed on the divided transmission surface 60*c*, a transmission interference membrane having a selected wavelength λ4 of 650 nm to 750 nm is formed on the divided transmission surface 60*d*, and a transmission interference membrane having a selected wavelength λ5 of 750 nm to 870 nm is formed on the divided transmission surface 60*e*.

Further, on the divided transmission surfaces 60*a* to 60*e*, outer peripheral portions 60*a'* to 60*e'* on outer peripheral side of the first region and inner peripheral portions 60*a"* to 60*e"* on inner peripheral side of the first region are the second region, and rays of any wavelength can be transmitted in the second region. An image 58 formed on the interference filter 15 stretches over the second region, the first region and over the second region, and a part of outer peripheral side of the image 58 is overlapped on the outer peripheral portions 60*a'* to 60*e'* and 60*f'*, and a part of inner peripheral side is overlapped on the inner peripheral portions 60*a"* to 60*e"* and 60*f"*.

In a case where the interference filter 15 is used, the divided transmission surface 60*f* is selected, and when the divided transmission surface is designed to concur with the optical axis, total transmission is performed without selecting the wavelength, and only a real image is acquired. Further, when one of the divided transmission surfaces 60*a* to 60*e* is selected, e.g. when the divided transmission surface 60*e* is selected among the formed images 58, wavelength selection is performed in a first regional portion 58*a* passing through the transmission interference membrane of the divided transmission surface 60*e*, and all rays are transmitted in a second regional portions 58*b* and 58*c* passing through the outer peripheral portion 60*e'* and the inner peripheral portion 60*e"*, and mixed image data is acquired, in which optical spectral image data acquired in the first regional portion 58*a* and real image data in the second regional portions 58*b* and 58*c* are acquired.

When wavelength range of optical spectra to be acquired is in the range of 400 nm to 870 nm, the divided transmission surface is sequentially changed over from the divided transmission surface 60*a* to the divided transmission surface 60*e*, and optical spectral image is acquired or each of the divided transmission surfaces 60 thus changed over.

As a result, by the rotation of the interference filter 15, wavelength can be selected in the range of 400 nm to 870 nm, and images can be acquired on the image pickup element 17 for each of the selected wavelengths, and a predetermined optical spectra can be acquired within the range of 400 nm to 870 nm.

When the number of divisions is determined to suit the wavelength of the optical spectrum to be acquired, and further, when the wavelength of the optical spectrum to be acquired is limited, optical spectrum may be acquired by selecting the corresponding divided transmission surfaces having the selected wavelength characteristics.

Further, as described above, the interference filter 15 is designed in form of a circular disk and to be rotatable, while the interference filter 15 may be designed in form of a long rectangular shape, and the divided transmission surface may be prepared by dividing the interference filter 15 in longitudinal direction. Then, the interference filter 15 is slid in longitudinal, direction and the divided transmission surfaces may be changed over.

Next, description will be given on the image pickup control device 21.

The image pickup control device 21 comprises an arithmetic control unit (CPU) 22, an image data recording unit 23, a camera controller 24, a camera control unit 25, a filter controller 26, a spectral data storage unit 27, an image synthesizing unit 28, an image processing unit 29, a characterstics extracting unit 31, a matching unit 32, a measuring unit 33, a model image forming unit 34, a display unit 35, and a storage unit 36.

The camera control unit 25 synchronously controls the camera 14, the interference filter 15, and an aperture 55. On the aperture 55, description will be given later. The filter controller 26 drives the motor 16 according to an instruction signal from the camera control unit 25, and rotates and determines a position of the interference filter 15 so that luminous fluxes pass through a predetermined divided transmission surface of the interference filter 15.

Further, based on the instruction signal from the camera control unit 25, the camera controller 24 acquires a signal to be emitted from the image pickup element 17. When the luminous fluxes pass through the divided transmission surfaces 60a to 60e of the interference filter 15, the mixed image data acquired are separated to real image data and to optical spectral image data of a predetermined wavelength, depending on the first regional portion 58a and the second regional portions 58b and 58c where the luminous fluxes pass through. The real image data thus separated are associated with the time of image pickup and are stored in the image data recording unit 23. The optical spectral image data are associated with the time of image pickup and are stored in the spectral data storage unit 27.

Further, in a case where the luminous fluxes pass through the divided transmission surface 60f of the interference filter 15, still image data comprising the real images only are acquired because both the first region and the second region are totally transmission surfaces. The still image data thus acquired are associated with the time of image pickup and are stored in the image data recording unit 23.

The image synthesizing unit 28 is to synthesize the optical spectral image data stored in the spectral data storage unit 27 according to an real image data of the second region stored in the image data recording unit 23. Further, the image synthesizing unit 28 is to synthesize the optical spectral synthesized image with the still image, and to prepare a hyper-spectral image having optical spectral information with all pixels of one image.

The image processing unit 29 has the characteristics extracting unit 31 and the matching unit 32, and the image processing unit 29 is to extract at least five or more of feature points (pass points) from an image data of one frame and to carry out tracking of image or matching of image according to the feature points regarding the image data, which are different in terms of time or regarding the image data acquired from different image pickup points.

For the image tracking and the image matching, SSDA method (sequential similarity detection algorithm), the normalized cross-correlation method, the least square matching method, etc. are used.

The measuring unit 33 is to carry out digital photogrammetry based on two image data acquired by the camera 14 from different image pickup positions and based on the positional data of image pickup position.

The model image forming unit 34 associates three-dimensional data of each of pixels measured by the measuring unit 33 with the hyper-spectral image, and prepares a model image, which has four-dimensional data (i.e. three-dimensional data+optical spectral image data).

In the storage unit 36, various types of programs are stored. These programs include: a program needed for camera control, a program needed for motor control, a program needed for synthesis of image data and optical spectral image data, a program needed for image tracking, a program needed for image processing, a program needed for measurement, a program needed for preparation of model image, a program for controlling the display unit 35, etc. The image data recording unit 23 and rue spectral data storage unit 27 may be prepared in a part of the storage unit 36.

Next, referring to FIG. 4 to FIG. 6, description will be given on an example of the camera 14 to be used in the present embodiment. The camera 14 as described below is designed in such manner that the optical spectra acquired by the divided transmission surfaces 60a to 60e of the interference filter 15 are further finely divided.

In FIG. 4, an optical system 45 of the camera 14 and the interference filter 15 provided on optical path of the optical system 45 are shown.

In FIG. 4, reference numeral 46 represents an optical axis of the optical system 45. Along the optical axis 46, an objective lens 47, a first relay lens 48, a second relay lens 49, a third relay lens 50, an image forming lens 51, and an image pickup element 52 are arranged. In FIG. 4, reference numeral 53 represents an image formed by the objective lens 47, and reference symbol "f" represents focal distance of the second relay lens 49.

The aperture 55 is disposed on the side closer to the second relay lens 49 of the first relay lens 48. The objective lens 47, the first relay lens 48, the second relay lens 49, the third relay lens 50, the image forming lens 51, the image pickup element 52, and the aperture 55 make up together the optical system 45.

The aperture 55 has an aperture orifice 55a in form of a slit and extending in a direction perpendicular to paper surface in the figure. The aperture 55 is disposed at a focal position closer to the object, or approximately at a focal position closer to the object, of the second relay lens 49. The aperture 55 is movably supported in a direction perpendicular to the optical axis 46 (i.e. in a direction perpendicularly crossing the aperture orifice 55a) so that the position of the aperture 55 can be changed adequately by a position changing means such as a linear motor etc.

In this case, the aperture 55 and the second relay lens 49 make up together a telecentric optical system 56. After passing through the first relay lens 48, luminous fluxes are split by the telecentric optical system 56 to a multiple of luminous fluxes (principal rays 57) running in parallel to each other.

A transmission type interference filter 15 with a plurality of transmission type interference membranes where different selected wavelength characteristics are prepared is provided on a converging position of the principal ray 57 (at an image-forming position or approximately at an image-forming position by the second relay lens 49). The interference filter 15 is rotatably supported on a rotation axis 59 and further can be rotated by a rotating means such as a motor etc. The interference filter 15 fulfills the function as a wavelength selecting filter. By light beams with specific wavelength after passing through the interference filter 15, an image is formed on the image pickup element 52 by the third relay lens 50 and the image-forming lens 51. The image thus formed will be a two-dimensional image with a specific wavelength.

The interference filter 15 has such property that wavelength selecting characteristics are changed according to incident angle of the light beams entering the interference filter 15. FIG. 5 shows a relation between an incident angle and the peak wavelength of the light, which passes through (i.e. dependency of the peak wavelength on the incident angle), and by changing the incident angle, it can be known that the peak wavelength is changing.

As shown in FIG. 4A, the aperture orifice 55*a* of the aperture 55 is positioned on the optical axis 46. In this case, the principal ray 57 runs in parallel to the optical axis 46. Next, in case the aperture 55 is moved as shown in FIG. 4B, —for instance, in case it is moved in upward direction as shown in the figure—, the principal ray 57 is tilted with respect to the optical axis 46. That is, incident angle to the interference filter 15 is changed. Therefore, by moving the aperture 55, the wavelength of the light passing through the interference filter 15 can be changed.

Figure 5:
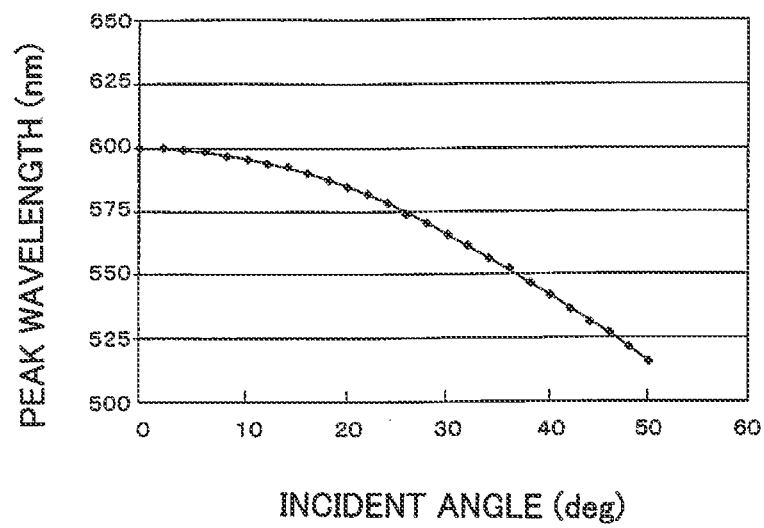
FIG. 5 is a graph to show a relation between an incident angle and a peak wavelength of a transmitting light.
Figure 6:
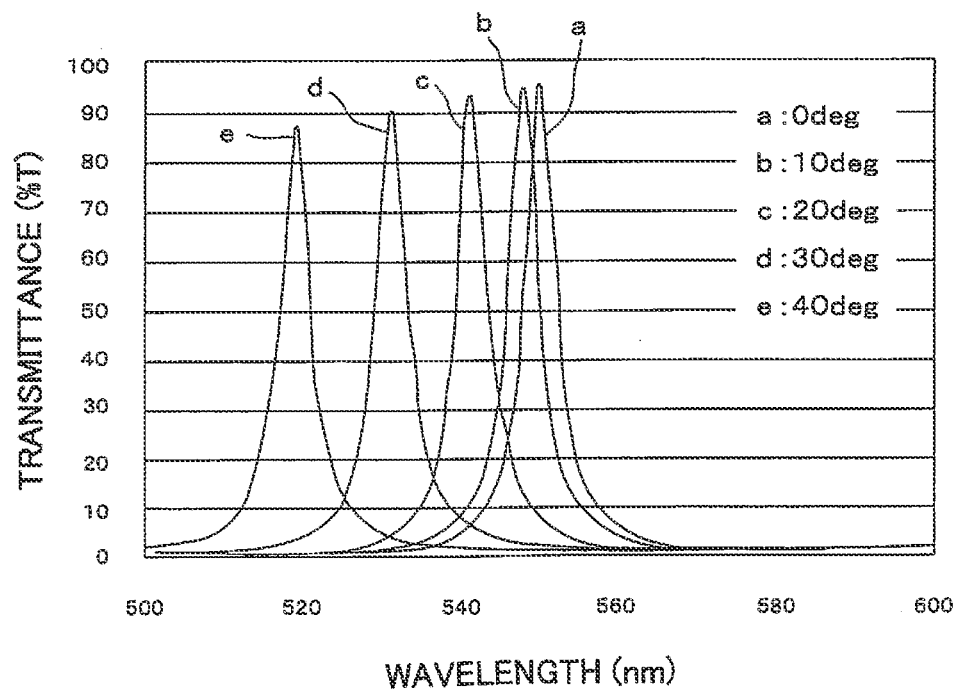
FIG. 6 is a graph to show wavelength transmitting characteristics to correspond to an incident angle to an interference filter.

Referring to FIG. 5, when the incident angle to the interference filter 15 is changed to the range of 0° to 50°, for instance, peak of the wavelength of the light passing through is changed to the range of 600 nm to 520 nm. This means that the interference filter 15 has wavelength selection range W of 600 nm to 520 nm. FIG. 6 shows wavelength transmission characteristics to match the incident angle to the interference filter 15. This represents an example of optical spectrum, which is acquired when the angle of the interference filter 15 is changed to 0°, 10°, 20°, 30° and 40° respectively.

In FIG. 4, the interference filter 15 is tilted with respect to the optical axis 46. As shown in FIG. 5, the incident angle dependency will be linear from a point where the incident angle exceeds 10°. Accordingly, by tilting the interference filter 15 in advance, the change of the selected wavelength with respect to the displacement of the aperture 55 can be effectively acquired.

Therefore, each time the aperture 55 is displaced by acquiring the image by the image pickup element 17 and by disposing the divided transmission surface 60 of the interference filter 15 having the wavelength transmission characteristics shown in FIG. 4 on an optical path of the principal ray 57, and optical spectrum in the wavelength range of 600 nm to 520 nm can be acquired. When the optical spectrum is acquired in the wavelength range exceeding the range of 600 nm to 520 nm, the interference filter 15 is rotated so that the divided transmission surface having a different wavelength selection range W' will be disposed on optical path of the principal ray 57. As described above, by combining the aperture 55 with the interference filter 15, it is possible to acquire the optical spectrum, which is derived by more finely dividing the optical spectrum acquired by the interference filter 15 itself.

Next, description will be given on operation in the present embodiment by referring to FIG. 7 and FIG. 8. In the following, description will be given on a case where the optical system. 45 having the interference filter 15 is used as the camera 14 and the camera 14 is mounted on the helicopter 1, which is a flying object.

While an image is acquired in hovering condition, posture of the camera 14 is always changing, and it is not in perfectly still stand state. Therefore, the image acquired for each of the wavelengths has some deviation. In this respect, if optical spectral image stored in the spectral data storage unit 27 is synthesized as it is, some problems arise, for instance, error may occur or blurring etc. may be caused.

FIG. 8 represents a condition where optical spectral images, each having selected wavelength of λ1, λ2, λ3 and λ4 respectively, are acquired in hovering state. Reference symbol S1 in FIG. 8A represents a condition where the image pickup device 11 is in completely standstill, and reference symbol S2 represents a condition where the image pickup device 11 moves in hovering state. FIG. 8B is a drawing where optical spectral images of λ1, λ2, λ3 and λ4 acquired when the image pickup device 11 are moving are developed in the course of time. In the figure, black circle represents a feature point extracted from images after passing through the transmission area of outer peripheral portions 60*a*' to 60*e*' and inner peripheral portions 60*a*'' to 60*e*'', which are the second region. As it is seen in FIG. 8A and FIG. 8B, when the images are synthesized as they actually are, the feature points do not concur with each other between the images, and it is seen that error has occurred or the images are blurred.

Accordingly, the matching (relative positioning) must be performed at the second region so that optical spectral image acquired for each of the wavelengths can be synthesized in the hovering state.

In the present embodiment, by rotation of the interference filter 15, still images containing only real images can be acquired. Also, by allowing the principal ray 57 to pass through the divided transmission surface 60*f*, and by allowing the principal ray 57 to pass through the divided transmission surfaces 60*a* to 60*e*, an optical spectrum image can also be acquired, and further, it is possible to acquire the real image when the principal ray 57 passes through the transmission area of outer peripheral portions 60*a*' to 60*e*' and the inner peripheral portions 60*a*'' to 60*e*'', the real images can also be acquired. Thus, it is possible to acquire mixed image data where these images are integrated together.

First, after the helicopter 1 is maintained in hovering state at a point O1 and is turned to standstill state, the interference filter 15 is rotated and the divided transmission surface 60*f* is selected. Then, a still image (a left image 42) is acquired at the point O1 via the divided transmission surface 60*f* by the camera 14, and a position of the point O1 is measured by the GPS device 9. The still image thus acquired is stored in the image data recording unit 23. Further, at least 5 or more feature points (preferably, more feature points) are extracted from the image data of the second regional portions 58*b* and 58*c* of the still image by the image processing unit 29.

After the still image is acquired at the point O1, the interference filter 15 is rotated, and the divided transmission surfaces 60*a* to 60*e* are sequentially changed over. Position of the aperture 55 is displaced for each time interval as required on each divided transmission surface, and mixed images are acquired each time the position of the aperture 55 is changed, and optical spectral images of λ1 to λn are acquired for each of the divided transmission surfaces respectively by a portion passing through the first regional portion 58*a*.

For instance, in a case where the divided transmission surface 60*a* is selected, optical spectral image of λa1 to λan are acquired. In a case where the divided transmission surface 60*b* is selected, optical spectral image of λb1 to λbn are acquired. In a case where the divided transmission surface 60*c* is selected, optical spectral image of λc1 to λcn are acquired. In a case where the divided transmission surface 60*d* is selected, optical spectral images of λd1 to λdn are acquired, and in a case where the divided transmission surface 60e is selected, optical spectral images of λe1 to λen are acquired.

By acquiring all of the optical spectral images as given above, optical spectral images of all wavelengths can be acquired. During the acquisition of the optical spectral images, at least 5 feature points are extracted from the real images acquired in the second regional portions 58b and 58c, and based on these feature points, tracking between the real images adjacent to each other in terms of time is carried out. Also, in a case where tilting or the like of the optical axis occurs between both of the real images until the next real image is acquired, coordinate conversion is carried out according to the feature point between both of the real images, and image matching is carried out.

In the real images separated from the mixed images, image pickup range is narrowed down. Because the real image is an image, which is taken in standstill state, displacement amount between the images is small, and tracking can be carried out on real images in narrower range.

Further, positional relation between the real image separated from the mixed image and the optical spectrum image is always constant, the condition acquired between the real images can be applied directly for the matching between the optical spectral images.

When the optical spectral images in all of the wavelengths at the point O1 have been acquired and the tracking between all of the real images has been completed, it is possible to carry out positioning and synthesizing of all of the optical spectral images without error according so tracking information of the real image.

Further, the optical spectral synthesized image and the first regional portion 58a of the still image at the point O1 are synthesized, and a hyper-spectral image is prepared.

When moving from the point O1 to the point O2 is started, the interference filter 15 is rotated first, and it is changed over to the divided transmission surface 60f. After the changing over of the interference filter 15, at least five feature points are extracted from the still images acquired at the point O1 first, and moving from the point O1 to the point O2 is started. During the moving from the point O1 to the point O2, the video images (frame images) are acquired by the camera 14 via the divided transmission surface 60f, and tracking of each of the frame images is carried out according to the feature points thus extracted. Because the real images can be acquired in the whole region of the divided transmission surface 60f, image tracking can be carried out to cope with bigger displacement.

When the point O2 is reached, a still image (a right image 43) at the point O2 is acquired by the camera 14 via the divided transmission surface 60f, and the position of the point O2 is measured by the GPS device 9. Next, by the image processing, unit 29, at least five of the feature points are specified on the still image at the point O2, and matching is carried out on a still image at the point O1 and on a still image at the point O2 based on the feature points. Further, by the measuring unit 33, digital photogrammetry is performed by the measuring unit 33 based on a still image acquired at the point O1 and on a still image acquired at the point O2 and on positional data of the point O1 and the point O2 measured by the GPS device 9, and three-dimensional data of each pixel is acquired.

Finally, three-dimensional data acquired at the point O1 and a hyper-spectral image acquired at the point O1 are synthesized, and a four-dimensional image including spectral data is prepared.

In the above, the hyper-spectral image is acquired at the point O1, while a hyper-spectral image can be acquired when the processing similar to the processing at the point O1 is performed on the point O2. As a result, the hyper-spectral image can be acquired at the point O2.

Accordingly, growing condition of the agricultural products can be identified from the optical spectral, or largeness of the agricultural products can be identified from three-dimensional data. Or, it is also possible to acquire information on the condition of ground surface containing the type of the substance exposed on the ground.

Figure 9:
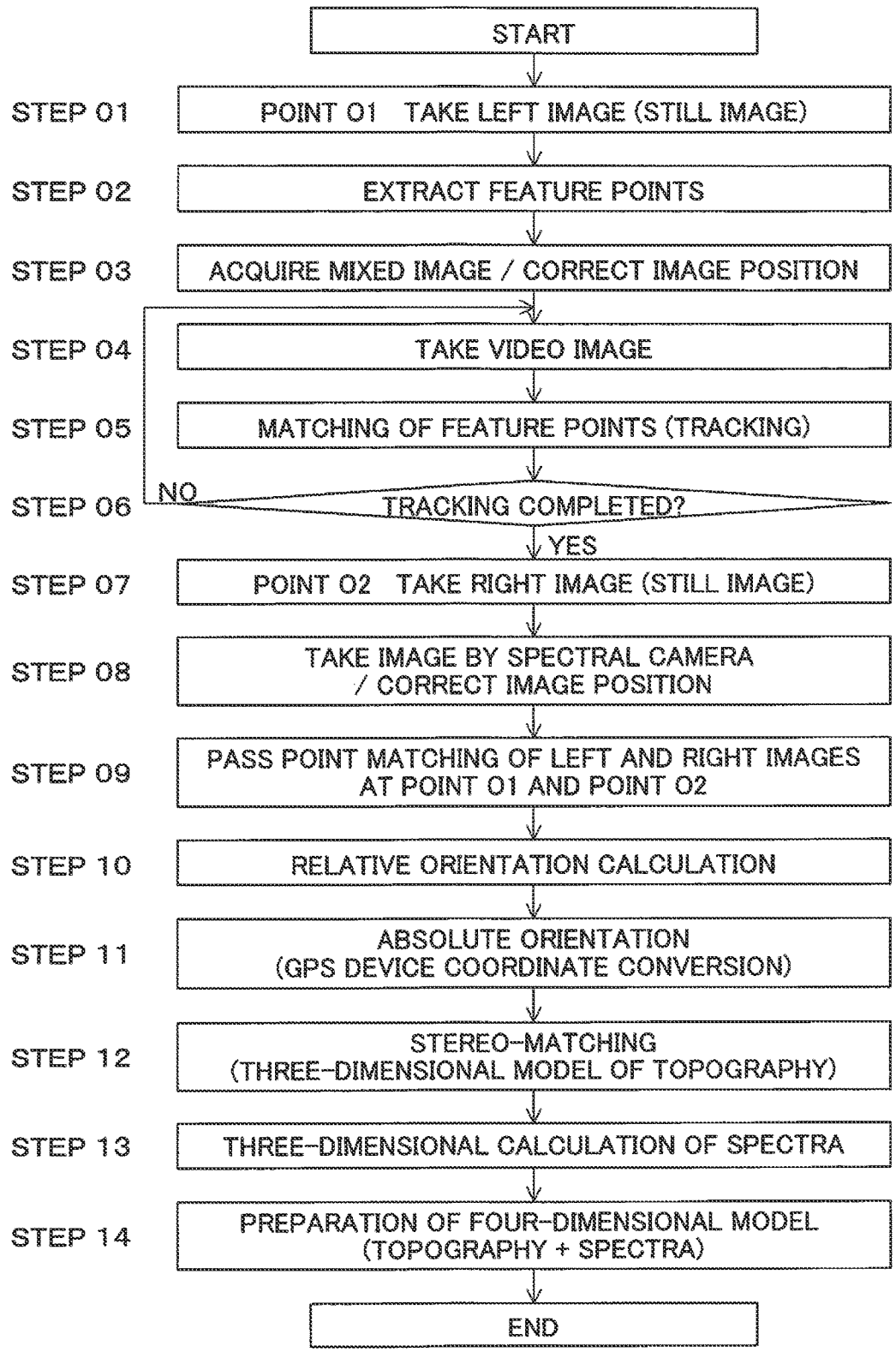
FIG. 9 is a flow chart to explain operation of the first embodiment of the present invention.
Figure 10:
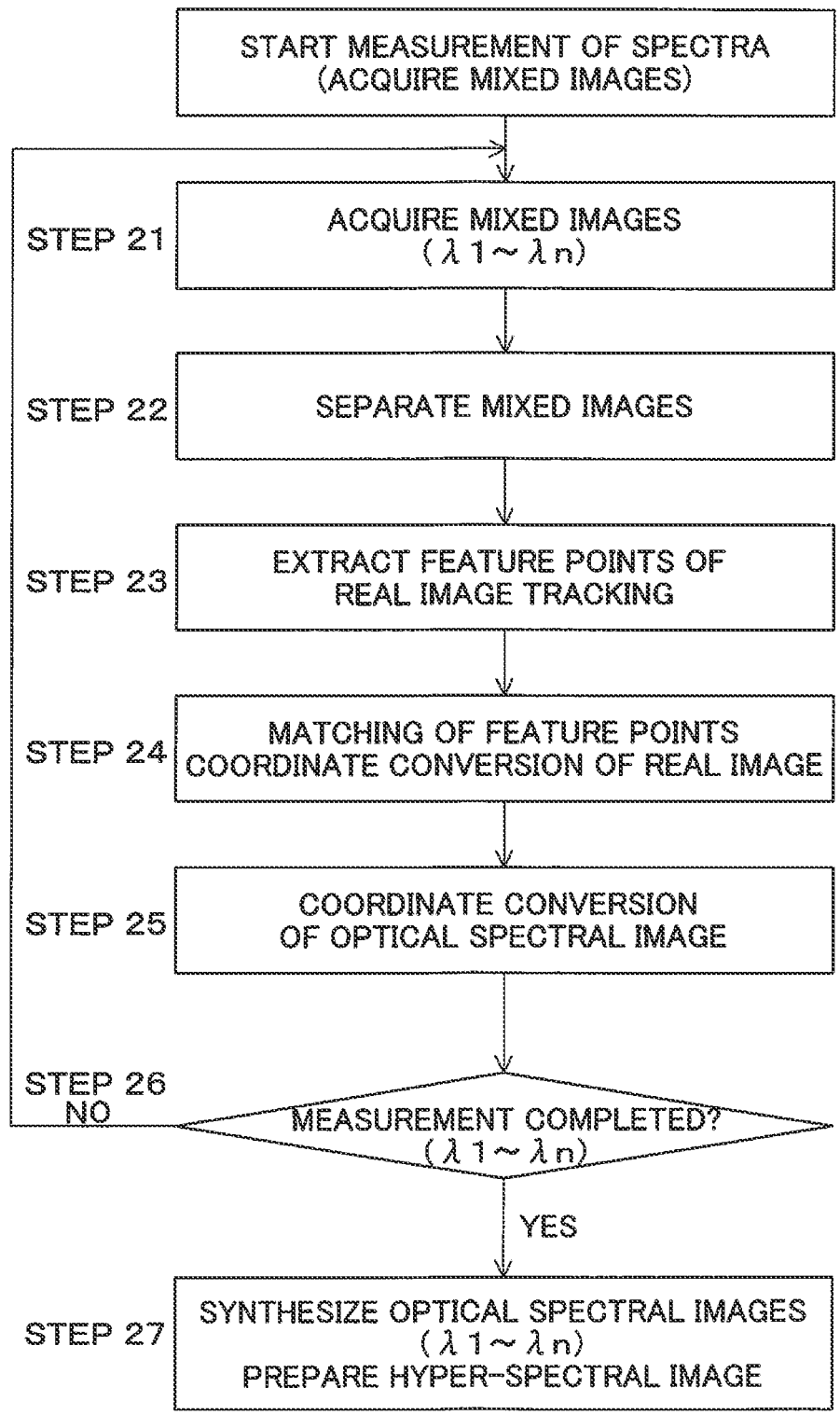
FIG. 10 is a flow chart to explain details of procedures in Step 03 to Step 06 as shown in FIG. 9.

Now, referring to FIG. 9 and FIG. 10, further description will be given on digital photogrammetry, acquisition and synthesis of optical spectral image and the hyper-spectral image as described above.

(Step 01) Hovering of the helicopter 1 is started at the point O1, and after the divided transmission surface 60f is selected by rotating the interference filter 15, the left image 42 is acquired by the camera 14 at the point O1. Then, measurement is performed on the position of the helicopter 1 (i.e. the point O1) by the GPS device 9.

(Step 02) Feature points are extracted by processing such as edge processing of the left image 42 acquired or by corner extraction processing etc.

(Step 03) Then, the interference filter 15 is intermittently rotated so that the principal ray 57 passes through predetermined regions of the divided transmission surfaces 60a to 60e. Further, the position of the aperture 55 is changed for each of the divided transmission surfaces, and a mixed image having optical spectral image and real image is acquired by the image camera 14 for each of the positions of the aperture 55. Also, the optical spectral image and the real image are separated from the mixed images acquired. Then, image tracking at the same position (hereinafter, referred as "the same position tracking") is performed by the separated real image. Based on the result of the same position tracking, correction of image position is carried out between each of the optical spectral images.

Description will be given on the acquisition of the optical spectral image at the point O1 and on the correction of image position in Step 21 to Step 27.

(Step 21) When spectrum measurement is started, mixed images having optical spectral image portion in the predetermined wavelength range (λ1 to λn) are acquired at the predetermined time interval for each wavelength.

(Step 22) The mixed image thus acquired is separated to an optical spectral image portion and a real image portion by the camera controller 24. The optical spectral image portion is stored in the spectral data storage unit 27 and the real image portion is stored in the image data storage unit 23 in time series.

(Step 23) By the image tracking (the same position tracking), at least five feature points are extracted from the real image portion (the first real image) as acquired at the same time as the separated optical spectral image portion (λ1), and feature point is identified in a real image portion (the second real image) as synchronized with the next optical spectral image portion (λ2), which is adjacent in terms of time.

(Step 24) Based on the feature point of the first real image portion and on the feature points of the second real image portion as acquired, matching is performed on the first real image portion and on the second real image portion, and coordinate conversion between the first real image portion and the second real image portion is carried out (Step 25) Because the real image portion and the optical spectral image portion are acquired at the same time, positional relation with the optical spectral image portion corresponding to the real image portion is always constant, and condition of the matching of the real image portion and condition of coordinate conversion are applied to the adjacent optical spectral image portion, which is adjacent in terms of time.

(Step 26) It is judged whether the optical spectral image portions of all wavelengths have been acquired or not. If not acquired yet, the procedure goes back to Step 21, and acquisition of the optical spectral image portion and the same position tracking are carried out.

(Step 27) When all optical spectral image portions are acquired for all of the wavelengths of the predetermined wavelength range ($\lambda 1$ to $\lambda n$), by synthesizing all of the optical spectral image portions according to the condition acquired by the tracking of the real image portion, a first optical spectral synthesized image having the optical spectrum of the predetermined wavelength range ($\lambda 1$ to $\lambda n$) at the point O1 can be acquired. Further, by synthesizing the first optical spectral synthesized image and the still image, a hyper-spectral image can be acquired.

(Step 04 to Step 06) When a still image and a hyper-spectral image at the point O1 are acquired, the helicopter 1 is moved to the point O2. During the moving, the interference filter 15 is rotated first, and the divided transmission surface 60f is selected. During the moving, video image is acquired by the camera 14, and image tracking (moving tracking) is carried out. The moving tracking may be carried out according to the feature points extracted on the left image 42 or the image tracking may be carried out during the moving by using the feature points finally acquired by the same position tracking in the hovering state.

(Step 07) When the helicopter 1 reaches the point O2 and the moving tracking is terminated, the hovering is started, and the right image 43, which is a still image, is acquired.

(Step 08) The interference filter 15 is rotated in the hovering state and the divided transmission surfaces 60a to 60e are selected. Further, the aperture 55 is displaced for each of the transmission surfaces, and a mixed image is acquired by the camera 14 for each of the positions of the aperture 55. Further, by the mixed images acquired, the optical spectral image portion and the real image portion are separated from each other. By the real image portion thus separated, image tracking at the same position (hereinafter, referred as "the same position tracking") is carried out. Based on the result of the same position tracking, correction of image position is carried out between each of the optical spectral image portions.

The procedures of Step 21 to Step 27 are carried out, and optical spectral image portions for all wavelengths of the predetermined wavelength range ($\lambda 1$ to $\lambda n$) at the point O2 are acquired. By synthesizing all of the optical spectral image portions thus acquired, the second optical spectral synthesized image having the optical spectrum of the predetermined wavelength range ($\lambda 1$ to $\lambda n$) at the point O2 are acquired. Further, by synthesizing the second optical spectral synthesized image with the right image 43, a hyper-spectral image is acquired.

(Step 09, Step 10 and Step 11) Based on the feature points identified on the right image 43 by the same position tracking, and also on the feature points identified in the left image 42, matching is performed. Then, coordinate conversion (relative orientation) with reference to either one of the left image 42 or the right image 43 is carried out. Further, coordinate conversion (absolute orientation) to geocentric coordinates of the GPS device 9 is performed.

(Step 12 and Step 13) Based on the results of absolute orientation, stereo-matching of the left image 42 and the right image 43 is carried out, and three-dimensional model of topography having three-dimensional positional data is acquired.

(Step 14) As described above, the mixed image and the still, image are taken on the same axis and are matched each other on 1:1 basis, and three-dimensional positional data at a position where spectral optical spectrum is acquired are acquired. By synthesizing the optical spectral image with the three-dimensional model, a four-dimensional model having three-dimensional positional data of topography and the optical spectral information can be acquired.

As described above, it is so arranged in the present embodiment that the interference filter 15 in form of a circular disk is provided on the camera 14 and a divided transmission surface divided at an angle as required in circumferential direction is prepared on the interference filter 15. Also, one of the divided transmission surfaces is designed to have a total transmission surface, where the rays of all wavelengths can pass through and both of the real image portion and optical spectral image portion can be acquired by a single camera. As a result, positioning of the optical spectral images can be carried out according to the real image, and even when the image pickup device is mounted on a mobile body such as the flying object 1 etc., an optical spectral synthesized image and a hyper-spectral image can be acquired with high accuracy. Further, there is no need to separately provide a spectral camera to acquire the optical spectral image besides a camera to acquire the real image and this contributes to the simplification of structure design and to the reduction of the cost.

Also, by providing the aperture 55, it is possible to have one or more optical spectra on a single divided transmission surface.

The second region where the principal ray 57 can totally pass through is prepared on a part of the divided transmission surface where interference membranes with different selected wavelength characteristics are formed. As a result, it is possible to acquire the optical spectral image portion and the real image portion at the same time. Even when deviation may occur over time between each of the images, the optical spectral image portion can be easily synthesized by the matching of the real image portion.

Further, because the divided transmission surface 60f is designed as a total transmission surface where the principal ray 57 can totally pass through, it is possible to acquire only the real images in wide range, and the image pickup device 11 according to the present embodiment can be applied in a processing, which requires extraction of a multiple of feature points such as moving picture tracking or the like.

In the optical, system 45, it is so designed that incident angle to the interference filter 15 is displaced by changing the position of the aperture 55, and the wavelength in a predetermined range can be changed. However, in a case where the wavelength of the optical spectrum to be acquired is already determined, and if kinds of the wavelength are few, the aperture 55 may not be used.

Figure 11A:
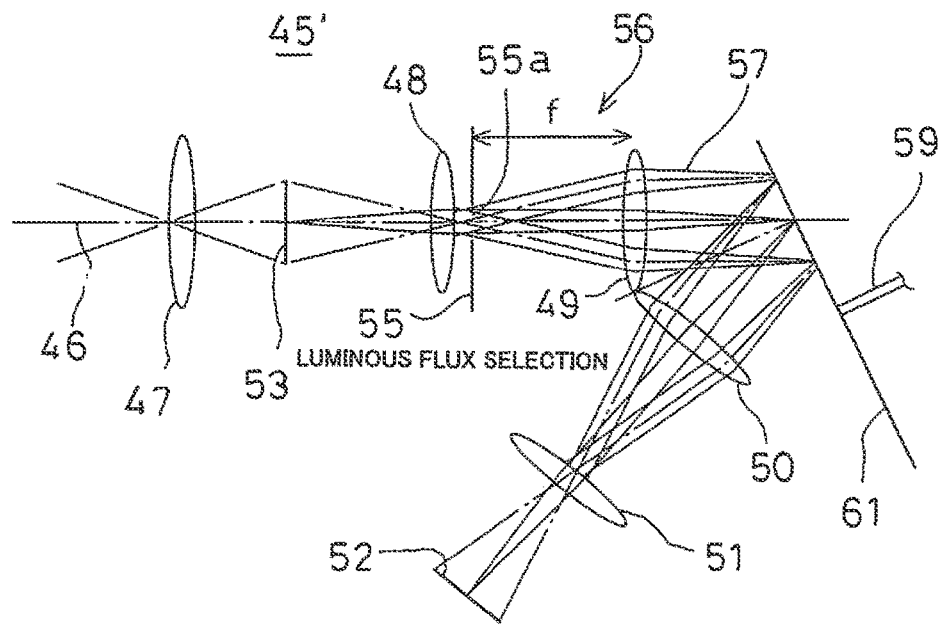
FIG. 11A and FIG. 11B are illustrations to show a camera to be used in a second embodiment of the present invention and to show an optical system having a reflection type interference filter.
Figure 11B:
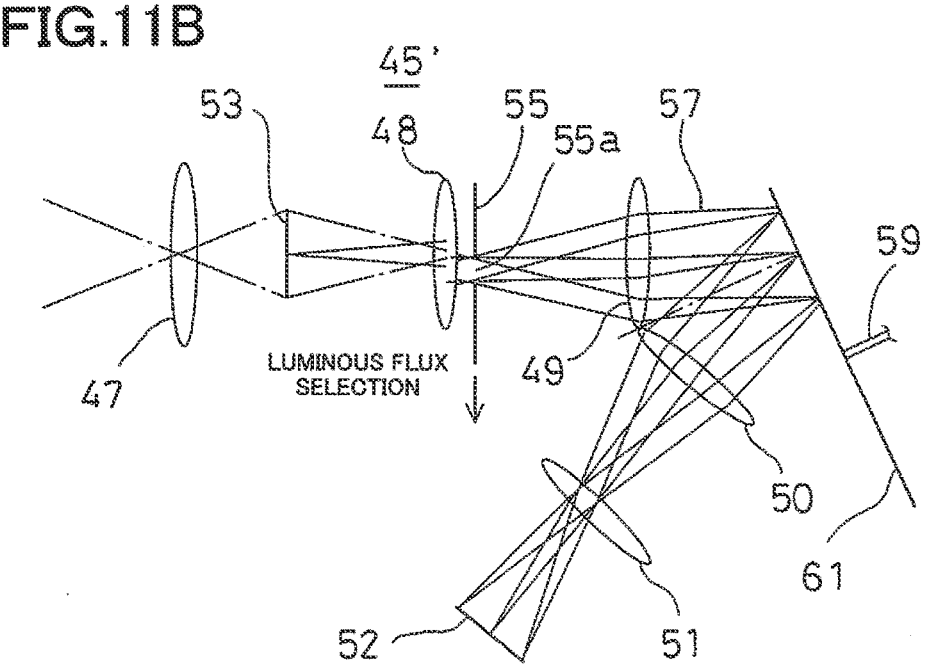
Figure 12:
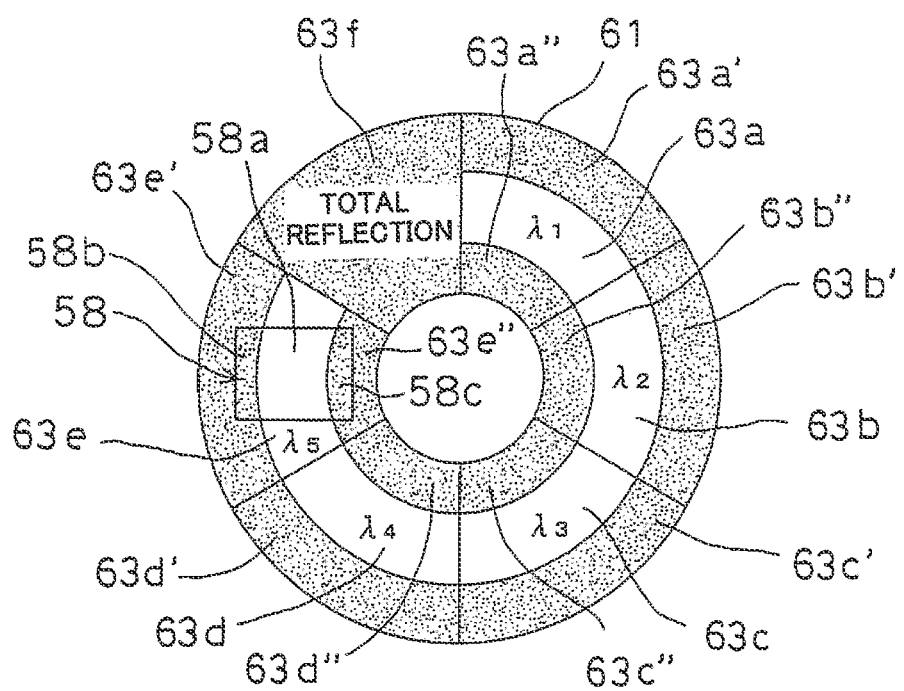
FIG. 12 represents a front view of an interference filter provided with a plurality of reflection interference membranes having different characteristics in a second embodiment.

FIG. 11 and FIG. 12 each represents an optical system 45' in a second embodiment of the present invention.

Figure 3:
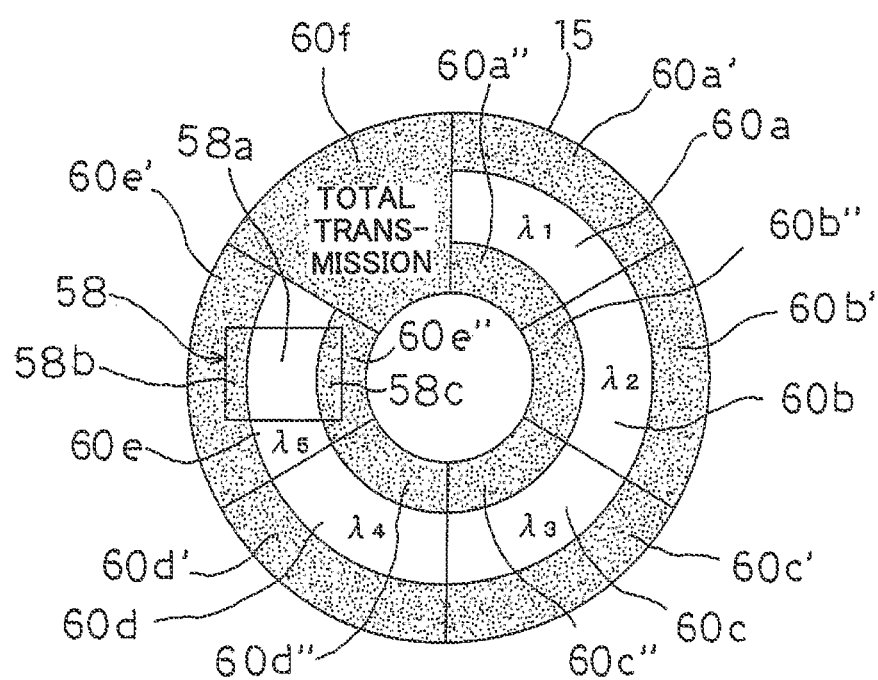
FIG. 3 is a front view of an interference filter provided with a plurality of transmission interference membranes with different characteristics according to the first embodiment.

In an optical system 45 as shown in FIG. 3, a transmission type interference filter 15 is used. As shown in FIG. 11, the optical system 45' may be prepared by using a reflection type interference filter 61, which is an optical characteristic changing unit. The interference filter 61 has reflection type interference membranes on a reflection mirror. It is rotatably supported around a rotation axis 59, and further it can be rotated by rotating means such as a motor etc. In the optical system 45', wavelength can be selected when the interference filter 61 reflects a principal ray 57.

In FIG. 11, the same component as in FIG. 4 is referred by the same symbol, and detailed description is not given here.

In the second embodiment as given above, too, by moving an aperture 55 as shown in FIG. 11B, incident angle of the principal ray 57 to the interference filter 61 is changed, and specific wavelength within the predetermined wavelength selection range W can be selectively reflected.

Further, as shown in FIG. 12, the interference filter 61 is designed in form of a circular disk. Reflection surface is equally divided at such angle as required in circumferential direction (divided into 6 equal parts in the figure), and divided portions are prepared as divided reflection surfaces 63a to 63f.

On the interference filter 61, among the divided reflection surfaces 63a to 63f, the divided reflection surfaces 63a to 63e, which are designed as a plurality of divided portions, a second region is prepared concentrically, a first region is prepared on inner side of the second region and further a second region is prepared concentrically on inner side of the first region. On the first region, a reflection type interference membrane, i.e. the first region having different selected wavelength characteristics of selected wavelengths $\lambda 1$ to $\lambda 5$, are prepared for each of the divided reflection surfaces 63a to 63e. Further, the divided reflection surface 63f, which is another divided portion, both the first region and the second region (63f' and 63f'') have no optical characteristics and can reflect the light beams of all wavelengths.

Further, on each of the divided reflection surfaces 63a to 63e, outer peripheral portions 63a' to 63e' on outer peripheral side of the first region and inner peripheral portion 63a'' to 63e'' on inner peripheral side are the second region. The second regions reflect the light beams of all wavelengths. An image 58 formed on the interference filter 61 stretches over the second region, the first region, and the second region. A part on outer peripheral side of the image 58 is overlapped on the outer peripheral portions 63a' to 63e' and 63f', and a part on inner peripheral side is overlapped on the inner peripheral portions 63a'' to 63e'' and 63f''.

The luminous fluxes reflected by the interference filter 61 form images on an image pickup element 52 via an image forming lens 51. When the interference filter 61 is used, the divided reflection surface 63f is selected, and when an optical axis 46 is designed to concur with the divided reflection surface 63f, the luminous fluxes are totally reflected without wavelength selection, and still image data having only real image data are acquired. In a case where one of the divided reflection surfaces 63a to 63e is selected, e.g. in case the divided, reflection surface 63e is selected, the luminous fluxes are reflected by a first regional portion 58a of the divided reflection surface 63e and wavelength is selected. Also, among the formed image 58, a part of the luminous fluxes is totally reflected in the second regional portions 58b and 58c, and mixed image data can be acquired.

As described above, by using a reflection type interference filter 61 as the interference filter, the optical system 45' can be designed in compact form.

Figure 13A:
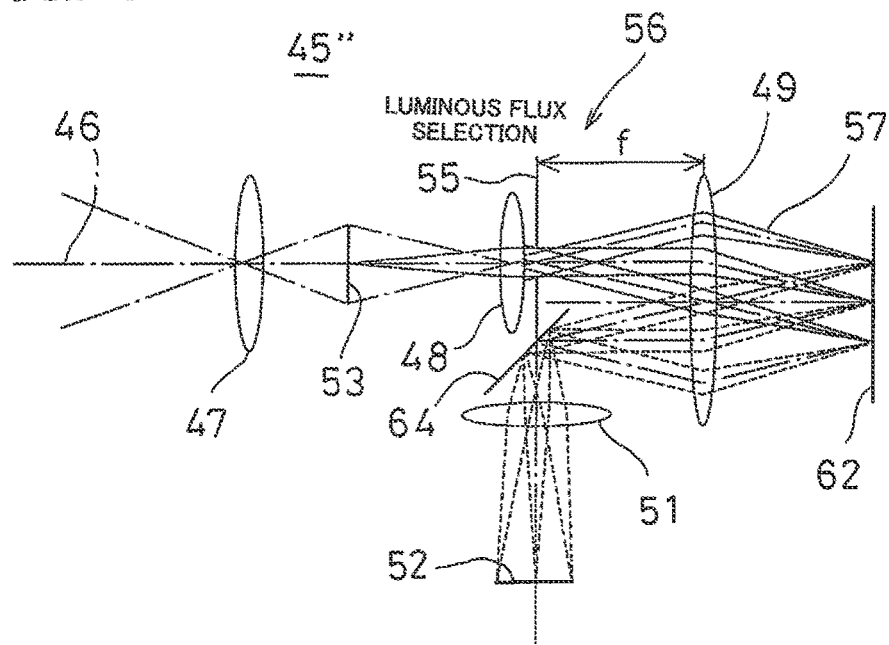
FIG. 13A and FIG. 13B are illustrations to show a variation example of the camera to be used in the second embodiment of the invention.

FIG. 13 shows a variation example of an optical system 45' shown in FIG. 11.

In the variation example shown in FIG. 13, a reflection type interference filter 62 is used, and the interference filter is designed in an arrangement similar to arrangement of an interference filter 61.

An objective lens 47, a first relay lens 48, and an aperture 55 are arranged along an optical axis 46. On an optical axis running in parallel to the optical axis 46 and separated by a predetermined extent, a second relay lens 49 is disposed and the interference filter 62 is disposed at a position opposite to the second relay lens 49. Luminous fluxes reflected by the interference filter 62 is deflected by a reflection mirror 64, and the luminous fluxes thus deflected run through an image forming lens 51 and forms an image on an image pickup element 52.

Figure 13B:
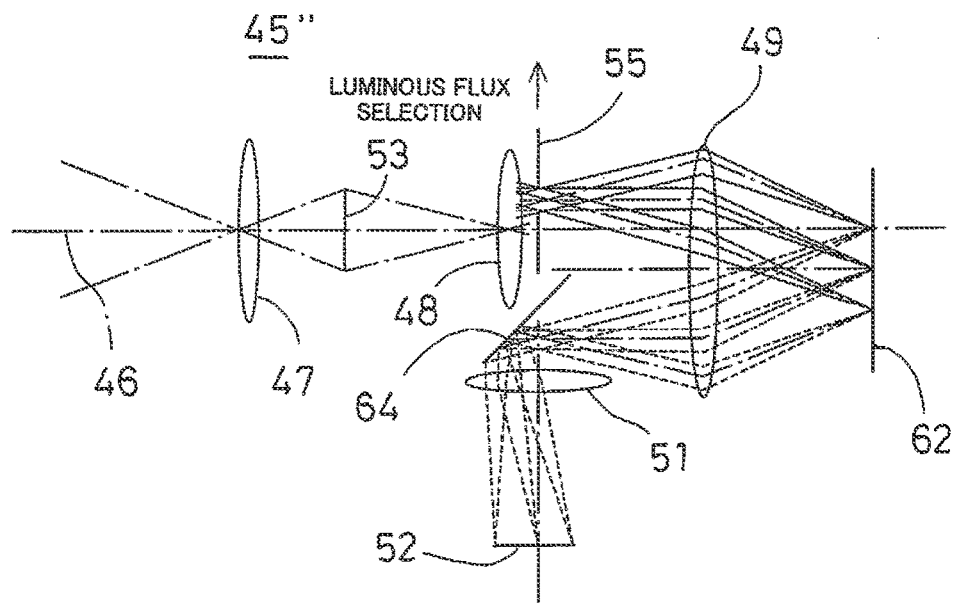

In this variation example, the first relay lens 48 and the aperture 55 are at such positions as deviated from the optical axis 46 of the second relay lens 49, and a principal ray 57 divided by a telecentric optical system 56 enters the interference filter 62 with tilting. Further, as shown in FIG. 13B, if the aperture 55 is moved so that the aperture 55 is separated from the optical axis 46, incident angle of the principal ray 57 will be still bigger. Therefore, by moving the aperture 55, the selected wavelength can be changed.

In the variation example as given above, the reflection type interference filter 62 is used. As a result, an optical system 45'' can be designed in compact form. Also, the second relay lens 49 is also used as a third relay lens 50 (see FIG. 11), and this contributes to the reduction of the number of component parts and to the reduction of the cost.

Next, referring to FIG. 14, description will be given on a third embodiment of the present invention.

Figure 14:
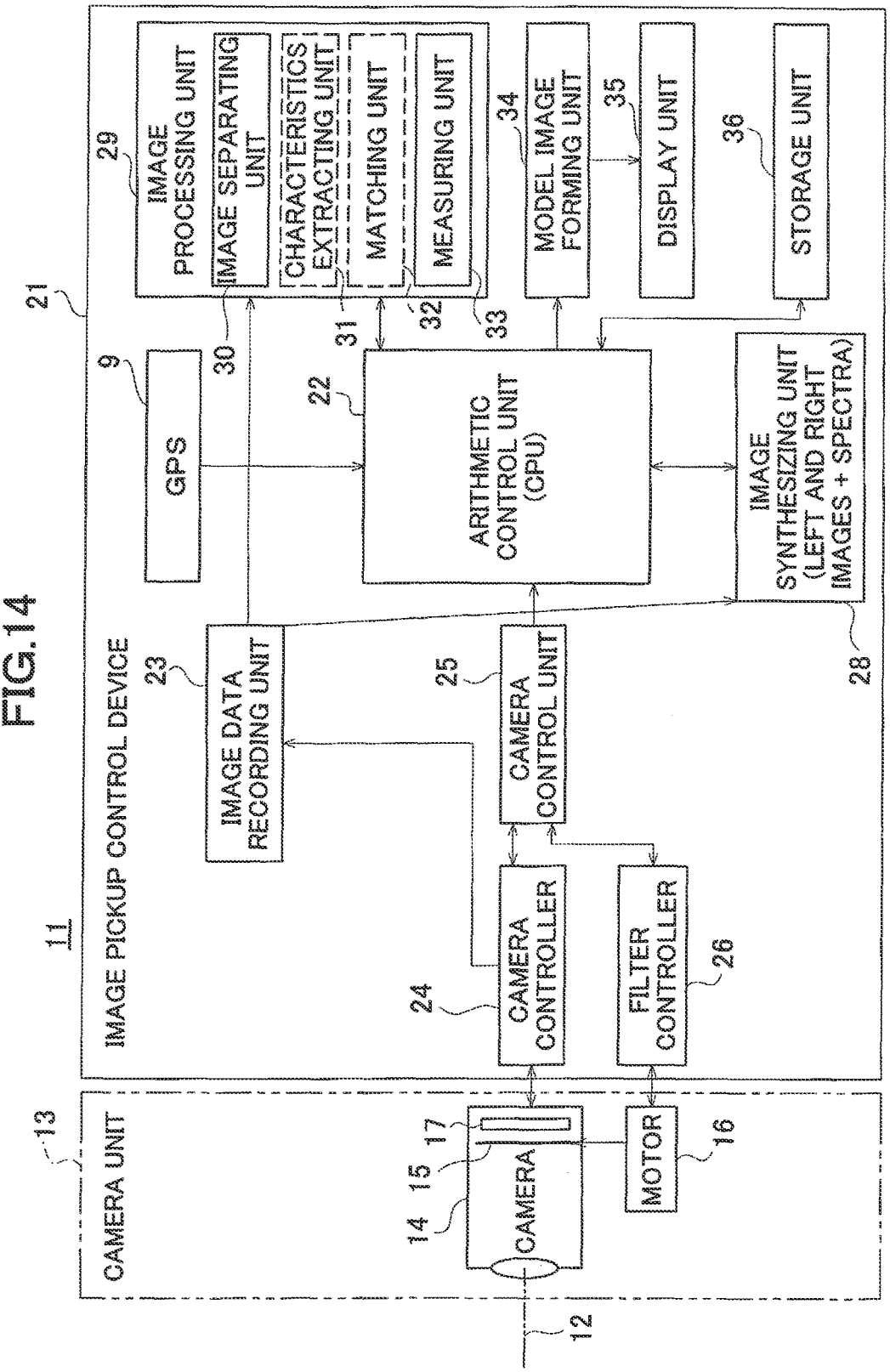
FIG. 14 as a schematical block diagram to show a camera unit and an image pickup control device of the image pickup device according to a third embodiment of the present invention.

FIG. 14 shows an approximate arrangement of an image pickup device 11 in the third embodiment. In this third embodiment, mixed image data as taken by a camera 14 are stored in an image data recording unit 23 without being separated to optical spectral image data and real image data by a camera controller 24.

In the mixed image data stored in the image data recording unit 23, at least three feature points are extracted from the real image portion, i.e. from second regional portions 58b and 58c (see FIG. 3), and matching is performed on the mixed image data, which are adjacent to each other in terms of time, based on the feature points.

The mixed image data are image data where the optical spectral image data and the real image data are integrated with each other. Positional relation between the optical spectral image data and the real image data in the mixed image data is always constant. Thus, when matching is carried out on the mixed image data based on the feature points, matching can be carried out automatically on the optical spectral images.

Finally, when the real image portion is separated from an image separating unit 30, an optical spectral synthesized image having optical spectrum in the predetermined wavelength range ($\lambda 1$ to $\lambda n$) can be acquired.

As described above, in the third embodiment, the extraction of the feature points of the real image portion and matching processing in the mixed image data function as the synthesizing processing of the optical spectral image data. As a result, it is possible to decrease the number of procedures in the processing, and this contributes to the reduction of the burden caused by the processing.

INDUSTRIAL APPLICABILITY

According to the present invention, an image pickup device comprises an optical characteristics changing unit, an optical system containing an objective lens and for leading a light from the objective lens to the optical characteristics changing unit, and an image pickup element for receiving a light via the optical characteristics changing unit, wherein the optical characteristics changing unit has two or more dividing units, and has a configuration where one of the dividing units is selectively disposed along an optical path, and the dividing unit has a first region to select a specific wavelength from the light coming from the optical system and a second region where optical characteristics of the light from the optical system are not changed. As a result, a real image without changing optical characteristics and an optical spectral image with changed optical characteristics can be acquired by using a single camera, and simplification of the structure and the reduction of the cost can be attained.

Further, according to the present invention, the image pickup device further comprises an image pickup control device, wherein based on image matching of an image taken via the second region of one dividing unit and an image taken via the second region of another dividing unit, an optical spectral synthesized image is prepared by synthesizing an image taken via the first region of the one dividing unit with an image taken via the first region of another dividing unit. As a result, matching condition between the images taken via the second region can be directly applied to an image taken via the first region.

Further, according to the present invention, the image pickup device further comprises an aperture disposed along an optical path, wherein the aperture has an aperture orifice, and wavelength to be selected by the optical characteristics changing unit can be changed by moving the aperture. As a result, optical spectrum in the predetermined wavelength range can be acquired without changing the optical characteristics changing unit.

Further, according to the present invention, in the image pickup device, the optical characteristics changing unit further comprises a still another dividing unit not to change optical characteristics of the first region and the second region. As a result, it is possible to acquire only the real images without changing optical characteristics and to carry out the video image tracking easily when the image pickup device is moved.

Further, according to the present invention, in the image pickup device, based on image matching of an image taken via the second region of two or more dividing units and a still image taken via the still another dividing unit, the image pickup control device synthesizes an image taken via the first region of two or more dividing unit and the still image and prepares a hyper-spectral image. As a result, hyper-spectral image can be easily acquired by a single camera.

Further, according to the present invention, the image pickup device further comprises a GPS device for carrying out measurement of geocentric coordinates, wherein the image pickup control device acquires a still image via the still another dividing unit at a first point, extracts two or more feature points from the still image at the first point, acquires a video image containing a frame image continuous in time series via the still another dividing unit during the moving from the first point to the second point, and further performs video image tracking by a video image moving from the first point to the second point, acquires a still image via the still another dividing unit at the second point, specifies the feature point on the still image at the second point, carries out stereo-matching of the still image at the first point and the still image at the second point based on the feature point, prepares a three-dimensional model based on positions in an geocentric coordinate system of the first point and the second point measured by the GPS device, and the image pickup control device prepares a four-dimensional model having three-dimensional position data and optical spectrum information by synthesizing the optical spectral synthesized image and the three-dimensional model. As a result, four-dimensional model can be easily acquired by using a single camera, and arbitrary three-dimensional position data and optical spectral information of an object to be measured can be readily acquired.

The invention claimed is:

1. An image pickup device, comprising an optical characteristics changing unit, an optical system containing an objective lens and for leading a light from said objective lens to said optical characteristics changing unit, and one image pickup element for receiving a light via said optical characteristics changing unit, wherein said optical characteristics changing unit has two or more dividing units, and has a configuration where one of the dividing units is selectively disposed along an optical path, and each of said dividing units has a first region to select a specific wavelength from the light coming from said optical system and a second region where optical characteristics of the light from said optical system are not changed,
wherein a part of said light and another part of said light pass through said first region and said second region respectively at the same time, wherein said image pickup element receives a light passing through said first region and a light passing through said second region at the same time and said image pickup element acquires an image which includes an optical spectral image part with a specific wavelength and an image part with no changing optical characteristics.

2. An image pickup device according to claim 1, further comprising an image pickup control device, wherein based on image matching of an image part taken via said second region of one dividing unit and an image part taken via said second region of another dividing unit, an optical spectral synthesized image is prepared by synthesizing an optical spectral image part taken via said first region of one dividing unit with an optical spectral image part taken via said first region of another dividing unit.

3. An image pickup device according to claim 1, further comprising an aperture disposed along an optical path, wherein said aperture has an aperture orifice, and wavelength to be selected by said optical characteristics changing unit can be changed by moving said aperture.

4. An image pickup device according to claim 1, wherein said optical characteristics changing unit further comprises a still another dividing unit not to change optical characteristics of said first region and said second region.

5. An image pickup device according to claim 4, wherein, based on image matching of an image taken via said second region of two or more dividing units and a still image taken via said still another dividing unit, said image pickup control device synthesizes image parts taken via said first regions of two or more dividing units and said still image and prepares a hyper-spectral image.

6. An image pickup device according to claim 5, further comprising a GPS device for carrying out measurement of geocentric coordinates, wherein said image pickup control device acquires a still image via said still another dividing unit at a first point, extracts two or more feature points from the still image at the first point, acquires a video image containing a frame image continuous in time series via said still another dividing unit during the moving from the first point to the second point, and further performs video image tracking by a video image moving from the first point to the second point, acquires a still image via said still another dividing unit at the second point, specifies said feature point on the still image at the second point, carries out stereo-matching of the still image at the first point and the still image at the second point based on said feature point, prepares a three-dimensional model based on positions in an geocentric coordinate system of the first point and the second point measured by said GPS device, and said image pickup control device prepares a four-dimensional model having three-dimensional position data and optical spectrum information by synthesizing said optical spectral synthesized image and said three-dimensional model.

7. An image pickup device according to claim 2, further comprising an aperture disposed along an optical path, wherein said aperture has an aperture orifice, and wavelength to be selected by said optical characteristics changing unit can be changed by moving said aperture.

8. An image pickup device according to claim 2, wherein said optical characteristics changing unit further comprises a still another dividing unit not to change optical characteristics of said first region and said second region.

9. An image pickup device according to claim 3, wherein said optical characteristics changing unit further comprises a still another dividing unit not to change optical characteristics of said first region and said second region.

10. An image pickup device according to claim 7, wherein said optical characteristics changing unit further comprises a still another dividing unit not to change optical characteristics of said first region and said second region.

11. An image pickup device according to claim 8, wherein, based on image matching of an image taken via said second region of two or more dividing units and a still image taken via said still another dividing unit, said image pickup control device synthesizes image parts taken via said first regions of two or more dividing units and said still image and prepares a hyper-spectral image.

12. An image pickup device according to claim 9, wherein, based on image matching of an image taken via said second region of two or more dividing units and a still image taken via said still another dividing unit, said image pickup control device synthesizes image parts taken via said first regions of two or more dividing units and said still image and prepares a hyper-spectral image.

13. An image pickup device according to claim 10, wherein, based on image matching of an image taken via said second region of two or more dividing units and a still image taken via said still another dividing unit, said image pickup control device synthesizes image parts taken via said first regions of two or more dividing units and said still image and prepares a hyper-spectral image.

14. An image pickup device according to claim 11, further comprising a GPS device for carrying out measurement of geocentric coordinates, wherein said image pickup control device acquires a still image via said still another dividing unit at a first point, extracts two or more feature points from the still image at the first point, acquires a video image containing a frame image continuous in time series via said still another dividing unit during the moving from the first point to the second point, and further performs video image tracking by a video image moving from the first point to the second point, acquires a still image via said still another dividing unit at the second point, specifies said feature point on the still image at the second point, carries out stereo-matching of the still image at the first point and the still image at the second point based on said feature point, prepares a three-dimensional model based on positions in an geocentric coordinate system of the first point and the second point measured by said GPS device, and said image pickup control device prepares a four-dimensional model having three-dimensional position data and optical spectrum information by synthesizing said optical spectral synthesized image and said three-dimensional model.

15. An image pickup device according to claim 12, further comprising a GPS device for carrying out measurement of geocentric coordinates, wherein said image pickup control device acquires a still image via said still another dividing unit at a first point, extracts two or more feature points from the still image at the first point, acquires a video image containing a frame image continuous in time series via said still another dividing unit during the moving from the first point to the second point, and further performs video image tracking by a video image moving from the first point to the second point, acquires a still image via said still another dividing unit at the second point, specifies said feature point on the still image at the second point, carries out stereo-matching of the still image at the first point and the still image at the second point based on said feature point, prepares a three-dimensional model based on positions in an geocentric coordinate system of the first point and the second point measured by said GPS device, and said image pickup control device prepares a four-dimensional model having three-dimensional position data and optical spectrum information by synthesizing said optical spectral synthesized image and said three-dimensional model.

16. An image pickup device according to claim 13, further comprising a GPS device for carrying out measurement of geocentric coordinates, wherein said image pickup control device acquires a still image via said still another dividing unit at a first point, extracts two or more feature points from the still image at the first point, acquires a video image containing a frame image continuous in time series via said still another dividing unit during the moving from the first point to the second point, and further performs video image tracking by a video image moving from the first point to the second point, acquires a still image via said still another dividing unit at the second point, specifies said feature point on the still image at the second point, carries out stereo-matching of the still image at the first point and the still image at the second point based on said feature point, prepares a three-dimensional model based on positions in an geocentric coordinate system of the first point and the second point measured by said GPS device, and said image pickup control device prepares a four-dimensional model having three-dimensional position data and optical spectrum information by synthesizing said optical spectral synthesized image and said three-dimensional model.

* * * * *